United States Patent [19]

Zink et al.

[11] 4,099,061
[45] Jul. 4, 1978

[54] TOMOGRAPHIC X-RAY APPARATUS FOR PRODUCING TRANSVERSAL LAYER IMAGES

[75] Inventors: Roderich Zink, Herzogenaurach; Walter Distler, Erlangen, both of Germany

[73] Assignee: Siemens Aktiengesellschaft, Berlin & Munich, Germany

[21] Appl. No.: 785,013

[22] Filed: Apr. 6, 1977

[30] Foreign Application Priority Data

May 13, 1976 [DE] Fed. Rep. of Germany ....... 2621308

[51] Int. Cl.² ............................................. G03B 41/16
[52] U.S. Cl. .................. 250/445 T; 250/402; 250/523
[58] Field of Search ............... 250/445 T, 523, 402

[56] References Cited

U.S. PATENT DOCUMENTS 4,001,593  1/1977  Wing ............................. 250/445 T Primary Examiner—Craig E. Church
Attorney, Agent, or Firm—Hill, Gross, Simpson, Van Santen, Steadman, Chiara & Simpson

[57] ABSTRACT

In an illustrated embodiment, the cables between the x-ray generator and the angularly movable x-ray source and between the angularly movable radiation detector and the processing circuitry are guided by means of an epicyclically movable planetary member operating between relatively rotatable inner and outer wheel members. The x-ray source and detector may be secured with the inner member which then may rotate through an angle of about 360° during a measurement operation. The cables may initially extend about substantially the entire perimeter of the inner member and then loop about the planetary member and be attached at a convenient point to the stationary outer member. The cables at one end could then extend from the inner member to the x-ray source and detector, and at the opposite end from the stationary outer member to the x-ray generator and other stationary circuit components. In this example, during rotation of the inner member with the x-ray source and detector, the cables are progressively unwound from the periphery of the inner member and transferred by the planetary member to the inner perimeter of the stationary outer member. In this way, the cables may be reliably guided during a 360° rotation of the measurement apparatus, for example. One or more further planetary members may be interposed between the inner and outer members in guiding relation to the cables.

6 Claims, 3 Drawing Figures

TOMOGRAPHIC X-RAY APPARATUS FOR PRODUCING TRANSVERSAL LAYER IMAGES

BACKGROUND OF THE INVENTION

The invention relates to a tomographic x-ray apparatus for producing transverse layer images of a radiographic subject with an x-ray measuring arrangement comprising an x-ray source producing a beam of x-rays penetrating the radiographic subject of which the cross-sectional extent perpendicular to the layer plane is equal to the layer thickness, and a radiation receiver which determines the intensity of radiation behind the subject, with a drive system for the measuring arrangement including a pivot mounting to produce rotational movements about a longitudinal axis running perpendicularly to the layer plane, a measured value converter for transforming the signals supplied by the radiation receiver into a layer image, and cables which join the measuring arrangement to an x-ray generator and the measured value converter.

A tomographic apparatus of this type is described in U.S. Pat. No. 3,778,614. In order to determine the layer image, the rotational movements may be made in small equidistant angular increments in alternating sequence with one linear scanning displacement each time, of the measuring arrangement along a straight line perpendicular to the central ray of the x-ray beam, if a single radiation detector is used as the radiation receiver. However, it is also a known fact that these linear scanning displacements are unnecessary if the radiation receiver is made up of a plurality of radiation detectors whose signals are processed simultaneously by the measured value converter, and if the x-ray beam is fan-shaped and impinges upon all the detectors simultaneously. In this case, a good image may be produced if the measuring arrangement is rotated about the patient through an angle of 380° during a measurement operation. The problem here is to run the cables for the measuring arrangement such that this rotation can proceed without disruption.

SUMMARY OF THE INVENTION

The object underlying the invention is to provide a tomographic x-ray apparatus of the type specified at the outset in which, with an angle of rotation of the order of magnitude of 360°, a trouble-free running of cables for the measuring arrangement is guaranteed over the entire angle rotation.

According to the invention, this object is achieved by virtue of the fact that the cables for the measuring arrangement are run in the form of a loop about a planetary pinion revolving between a rotatably mounted sun wheel and a stationary hollow wheel, that, on the one hand, the cables are attached to the sun wheel and on the other hand, to the hollow wheel, and that the cable length between the two cable attachment points corresponds to the desired angle of rotation of the measuring arrangement. In the case of the tomographic x-ray apparatus of the invention, the planetary pinion ensures a perfect cable guidance while the measuring arrangement is rotating.

It is particularly expedient to dispose, at a distance from the planetary pinion having the cable directly wrapped thereon, at least one further pinion in the cable loop for guiding the cables.

Other objects, features and advantages of the present invention will be apparent from the following detailed description taken in connection with the accompanying sheet of drawings.

DETAILED DESCRIPTION

Figure 1:
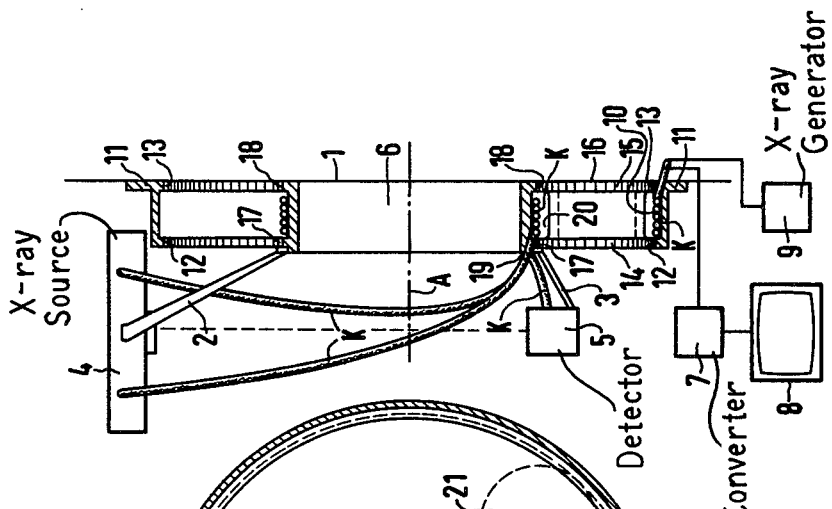
FIG. 1 is a somewhat diagrammatic longitudinal sectional view of a cable guiding arrangement in accordance with the present invention and also indicating diagrammatically other components of the tomographic x-ray apparatus.
Figure 2:
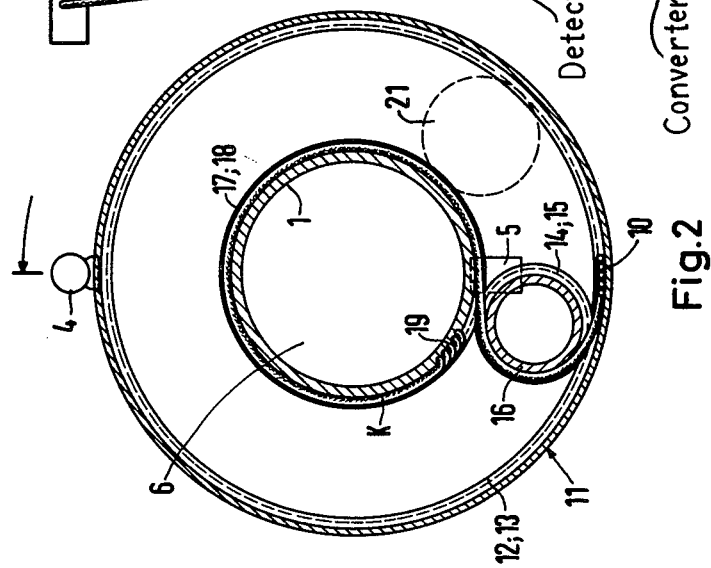
FIG. 2 is a somewhat diagrammatic transverse sectional view showing the cable guiding arrangement in its extreme counterclockwise position.

Represented in FIGS. 1 and 2 is a sun wheel 1 to which is attached, by means of two supports 2 and 3, an x-ray measuring arrangement comprising an x-ray tube 4 and a radiation detector whose central portion is diagrammatically indicated at 5. The sun wheel 1 has a central opening 6 into which a patient may be moved, for examination by the measuring apparatus 4, 5. The x-ray tube 4 emits a fan-shaped beam of x-rays and the detector 5 consists of a series of detector units which are disposed to be simultaneously impinged by respective segments of the fan-shaped x-ray beam. The angular extent of the fan-shaped x-ray beam is here selected such that a complete transverse layer of the patient is penetrated by x-radiation and the detector 5 may have a corresponding arcuate extent (with a center of curvature at the focus of the x-ray tube 4, for example). The thickness of the examined body layer is here equal to the cross-sectional extent of the x-ray beam perpendicular to the layer plane. To examine the patient, the measuring arrangement 4, 5, is rotated around the patient with sun wheel 1 rotating through approximately 360° about the axis A. A measured value converter linked to the detector 5 here computes from the signals of the detector 5 the image of the examined body layer, and this image is reproduced on a display unit 8. The x-ray tube 4 is supplied by an x-ray generator 9.

The cables K for the x-ray tube 4 and the detector 5 are run at point 10 into a stationary hollow wheel or outer member 11 disposed concentrically to the sun wheel or inner member 1 and are there attached to it. The hollow wheel 11 has two drive transmission means or gear tooth formations 12, 13, spaced apart from one another in the axial direction; and cooperating drive transmission means or gear tooth formations 14, 15 of a planet pinion or planetary member 16 are in driven engagement therewith. The drive transmission means 14, 15 of planetary member 16 are also in engagement with drive transmission means 17, 18 of the sun wheel or inner member 1. The cables K are run in the form of a loop about the planet pinion 16 and are attached to the sun wheel 1 at point 19. The cable length between the two cable attachment points 10 and 19 is selected to suit the desired angle of rotation of the measuring arrangement 4, 5. The cables K lie in a groove 20 of the planet pinion 16 between the drive transmission means or serrated rims 14, 15, and in corresponding grooves of the sun wheel 1 and the hollow wheel 11 between the serrated rims 17, 18 and 12, 13.

Figure 3:
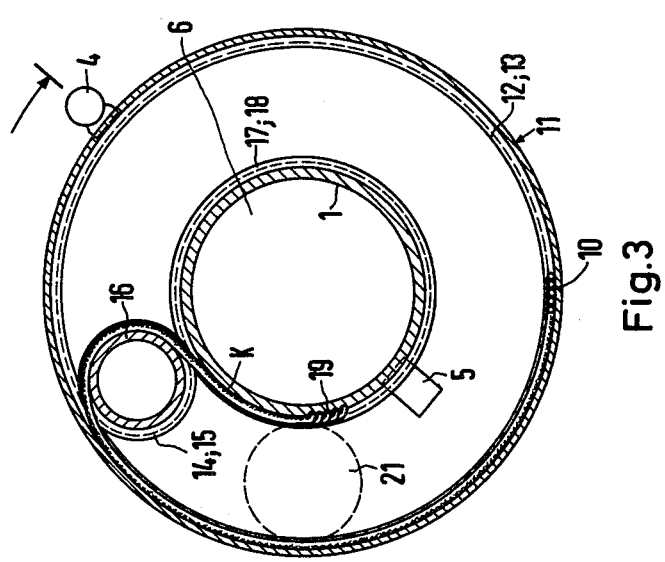
FIG. 3 is a transverse sectional view similar to that of FIG. 2 but illustrating the cable guiding apparatus approaching its extreme clockwise rotational position.

FIG. 2 shows the position of the measuring arrangement 4, 5 in one of its extreme positions (with sun wheel 1 in its extreme counterclockwise position) in which the cables K are almost wound about the sun wheel 1. FIG. 3 shows the measuring arrangement 4, 5 in its other extreme position, in which in comparison with FIG. 2, the cables K are largely unwound from the sun wheel 1. Comparison of FIGS. 2 and 3 shows clearly that, with the described arrangement for running or guiding the cables, an angle or rotation of more than 360° for the measuring arrangement 4, 5, is possible with the aid of the planet pinion 16.

A particularly good method of running the cables is achieved if a further planet pinion 21 is disposed at a distance from the planet pinion 16—as indicated in FIGS. 2 and 3 by broken lines. Still further planet pinions may be added within the scope of the invention.

It will be apparent that many modifications and variations may be effected without departing from the scope of the novel concepts and teachings of the present invention.

We claim as our invention:

1. Tomographic x-ray apparatus for producing transverse layer images of a radiographic subject with an x-ray measuring arrangement comprising an x-ray source producing a beam of x-rays for penetrating the radiographic subject, and a radiation receiver for determining the intensity of radiation beyond the subject, with a pivot mounting accommodating rotational movement of the measuring arrangement about an axis running perpendicular the layer plane, with a measured value converter for transforming the signals supplied by the radiation receiver into a layer image, and with cable means which join the measuring arrangement to an x-ray generator and to the measured value converter, characterized in that cable guiding means are provided comprising an epicyclically movable planetary member with inner and outer relatively rotatable members in driving relation to the planetary member, said cable means forming a loop about said planetary member and being attached to the rotatable members such that the cable means is fed from the inner member about the planetary member to the outer member in one direction of relative rotation of the inner and outer members, and is fed from the outer member about the planetary member to the inner member in the opposite direction of relative rotation of the inner and outer members.

2. Apparatus according to claim 1 with the outer member having means for storing the cable means along the inner periphery thereof as the cable is fed thereto from the planetary member during relative rotation in said one direction of the inner and outer members.

3. Apparatus according to claim 1 with the members having drive transmission means at each of the axially opposite margins thereof providing for the drive of the planetary member during relative rotation of the inner and outer members.

4. Apparatus according to claim 3 with said cable guiding means having groove means between the drive transmission means for accommodating the cable means.

5. Apparatus according to claim 1 with the inner member being rigidly connected to the measuring arrangement and having a central opening for receiving a patient.

6. Apparatus according to claim 1 with the cable guiding means comprising at least one further planetary member disposed in driven relation to the inner and outer members and in guiding relation to the cable means.

* * * * *